(12) United States Patent
Hollern

(10) Patent No.: US 9,289,320 B2
(45) Date of Patent: Mar. 22, 2016

(54) INFLATABLE CERVICAL COLLAR

(71) Applicant: Megan Hollern, Clearwater, FL (US)

(72) Inventor: Megan Hollern, Clearwater, FL (US)

( * ) Notice: Subject to any disclaimer, the term of this patent is extended or adjusted under 35 U.S.C. 154(b) by 136 days.

(21) Appl. No.: 14/147,275

(22) Filed: Jan. 3, 2014

(65) Prior Publication Data

US 2015/0190266 A1     Jul. 9, 2015

(51) Int. Cl.
*A61F 5/00* (2006.01)
*A61F 5/055* (2006.01)

(52) U.S. Cl.
CPC .......... *A61F 5/055* (2013.01); *A61F 2250/0003* (2013.01)

(58) Field of Classification Search
CPC   B63C 9/1255; B63C 11/30; B63C 2009/085; B63C 9/08; B63C 11/2245; B63C 2011/306; B63C 9/1055; B63C 9/155; B63C 2009/0094; B63C 2009/042; B63C 2009/044; B63C 2009/131; B63C 9/0005; B63C 9/20; B63C 11/08; A61F 7/10; A61F 2007/0018; A61F 7/00; A61F 2007/0008; A61F 2007/0009; A61F 2007/0042; A61F 2007/0056; A61F 2007/0238; A61F 7/03; A61F 7/08; A61F 7/106; A61F 2007/0058; A61F 5/34
USPC ............................... 602/17–18; 128/DIG. 23
See application file for complete search history.

(56) References Cited

U.S. PATENT DOCUMENTS

| 3,071,133 | A  | * | 1/1963  | Eisen ............................. 602/13 |
| 7,048,705 | B2 | * | 5/2006  | Pillai .............................. 602/18 |
| 8,920,351 | B2 | * | 12/2014 | Polliack et al. ................. 602/19 |
| 2003/0158015 | A1 | * | 8/2003 | Watson ........................... 482/10 |

* cited by examiner

*Primary Examiner* — Michael Brown

(57) ABSTRACT

A cervical collar having a body with an anterior side, a posterior side, an upper portion and a lower portion is provided. The cervical collar may include a chin support that is formed at the upper portion of the anterior side of the body. The present invention may further include an inflatable pocket formed on the posterior and lateral sides of the body. The cervical collar may be wrapped around a neck of a user so that the chin support aligns and supports the chin of the user. The inflatable pocket may be inflated with a gas or a liquid to further support the neck of the user.

9 Claims, 2 Drawing Sheets

INFLATABLE CERVICAL COLLAR

BACKGROUND OF THE INVENTION

The present invention relates to a cervical collar and, more particularly, to an inflatable cervical collar.

Current cervical collars (c-collars) have a generic curvature of the posterior cervical spine and chin piece, and therefore do not directly support the spine, allowing for excessive head and neck movement. Most c-collars, even if fitted appropriately, still allow for undesirable movement of the neck due to space not voided within the c-collar. As a result, there is a possibility of the patient's degree of cervical spinal curvature to alter when changing positions, during extrication, securing the patient on a backboard, or other manipulative movements.

As can be seen, there is a need for a cervical collar that form fits to the user's neck for further support.

SUMMARY OF THE INVENTION

In one aspect of the present invention, a cervical collar comprises: a body comprising an anterior side, a posterior side, and lateral sides, an upper portion and a lower portion, wherein the body is configured to wrap around a user's neck; a connector releasably attaching the anterior side and the posterior side; a chin support formed at the upper portion of the anterior side; and an inflatable pocket formed on the body of the cervical collar.

In another aspect of the present invention, the inflatable pocket is formed on at least one of the posterior and lateral sides, the cervical collar further comprises a tubing comprising a first end and a second end, wherein the first end is attach to an entrance of the inflatable pocket and the second end forms an inlet configured to receive at least one of a gas and a liquid that flows through the tubing and inflates the inflatable pocket, wherein the tubing is embedded within the body of the cervical collar and wherein the inlet forms an end adapter inlet at a surface of the body, wherein the end adapter inlet is configured to receive a syringe or syringe-like device. The cervical collar further comprises a viscoelastic polyurethane foam lining the chin support, wherein the chin support comprises a top end and a bottom end, wherein the foam tapers from the top end to the bottom end, wherein a thickest portion of the foam is at the top end, wherein the body is adjustable in height.

In another aspect of the present invention, a method of securing a cervical collar to a patient comprises: providing a cervical collar comprising a body comprising an anterior side, a posterior side, and lateral sides with an inflatable pocket formed on at least one of the posterior and lateral sides; wrapping the body of the cervical collar around a user's neck and connecting the anterior side and the posterior side together; and inflating the pocket with at least one of a gas and a liquid, wherein the pocket is inflated so that the body of the cervical collar is pressing against the user's neck.

These and other features, aspects and advantages of the present invention will become better understood with reference to the following drawings, description and claims.

DETAILED DESCRIPTION OF THE INVENTION

Figure 1:
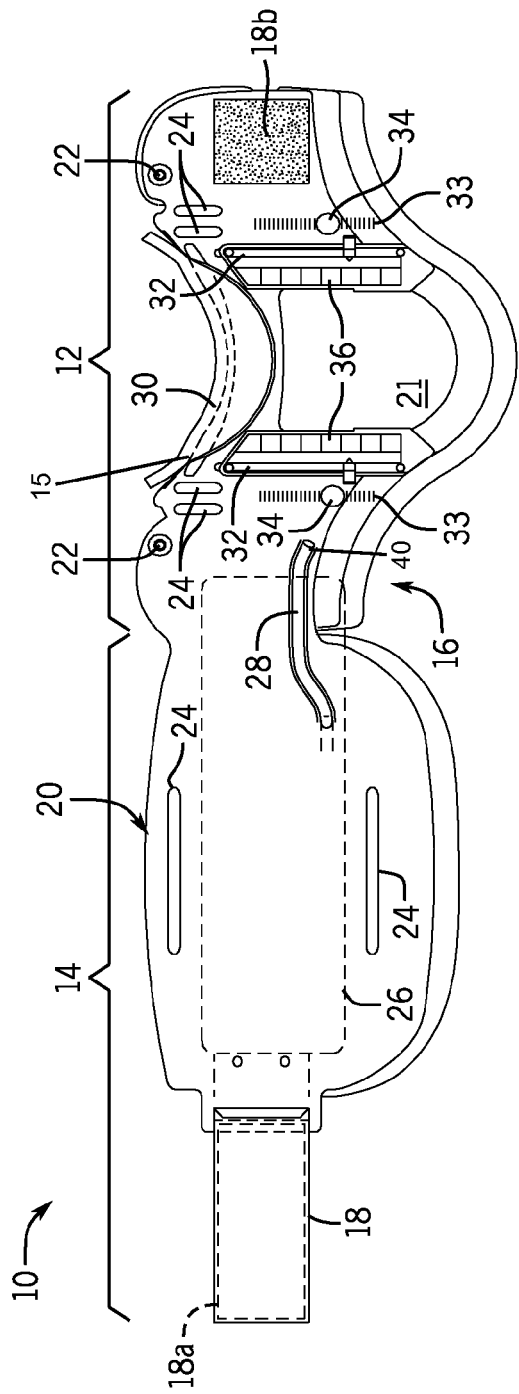
FIG. 1 is a front elevation view showing the outside of the present invention in an open position.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a cervical collar having a body with an anterior side, a posterior side, lateral sides an upper portion and a lower portion. The cervical collar may include a chin support that is formed at the upper portion of the anterior side of the body. The present invention may further include an inflatable pocket formed on the posterior side of the body extending to the lateral sides. The cervical collar may be wrapped around a neck of a user so that the chin support aligns and supports the chin of the user. The inflatable pocket may be inflated with a gas or a liquid to further support the neck of the user.

The present invention includes a height adjustable cervical spinal restriction device with an inflatable posterior-lateral pocket and moldable foam under jaw. The present invention further restricts spinal motion in the lateral, flexion, and extension motions of the neck with the combination of an inflatable posterior-lateral pocket, moldable foam around the chin and jaw, and altering height adjustments. The posterior-lateral pocket may also increase patient comfort by acting as a built in pillow. The present invention facilitates a more properly fitted cervical collar, customized support for the patient's curvature of the neck, and overall enhanced cervical spinal motion restriction.

In certain embodiments, the present invention may include moldable foam around the chin. Further, the foam may include varying thicknesses around the chin of the c-collar. For example, the foam in the bottom center of the chin may be the thinnest, and the foam may increase in thickness towards the lateral sides of the chin. This increase in foam thickness and moldable or forming foam adjusts to different chin lengths, widths, and curvatures of each individual person's chin or anatomy. Therefore, the tapered foam creates a more exact and supportive fit of the c-collar around the chin, which is important particularly for improved lateral cervical spinal motion restriction.

As current c-collars today are more rigid, flat, or not specifically designed for each person's curvature of the cervical spine, along with a chin and jaw piece with one consistent width or thickness of foam, a person is still able to move in lateral, or side to side motions, and flexion and extension motions of the neck due to a generic fit, even with the c-collar sized and properly fitted to the patient. There is a lack of padding and voiding of spaces within the c-collar. The present invention may reduce or remove the posterior and lateral spaces. The present invention, which includes the c-collar with molded foam chin piece for lateral support and properly filled posterior to lateral pocket further restricts and prevents the lateral, flexion and extension motions of the neck.

Figure 2:
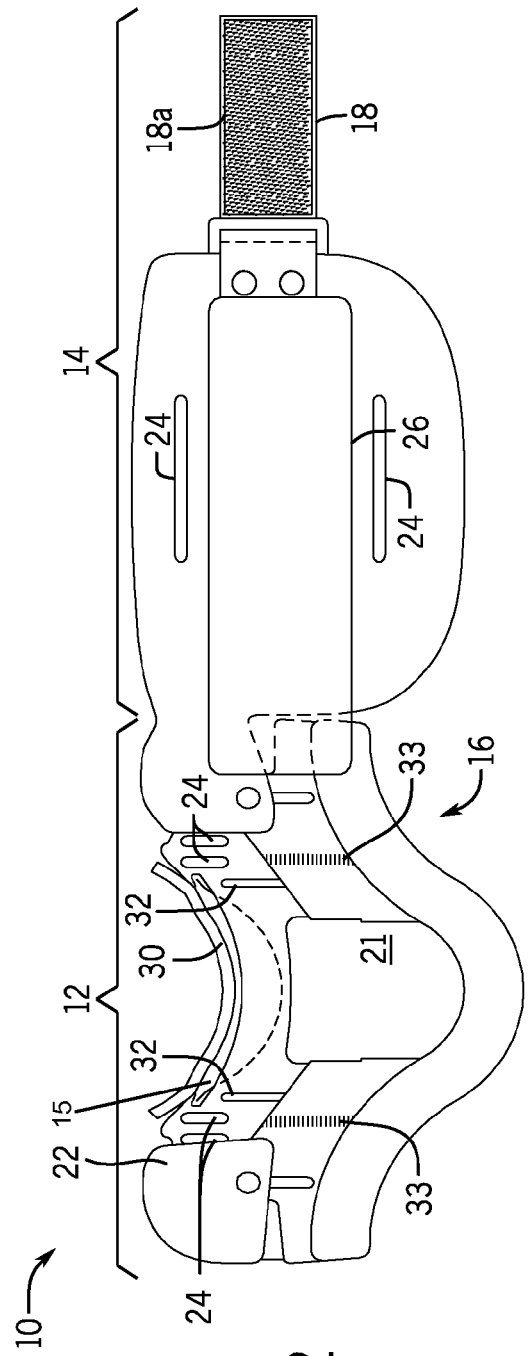
FIG. 2 is a rear elevation view showing the inside of the present invention in an open position.
Figure 3:
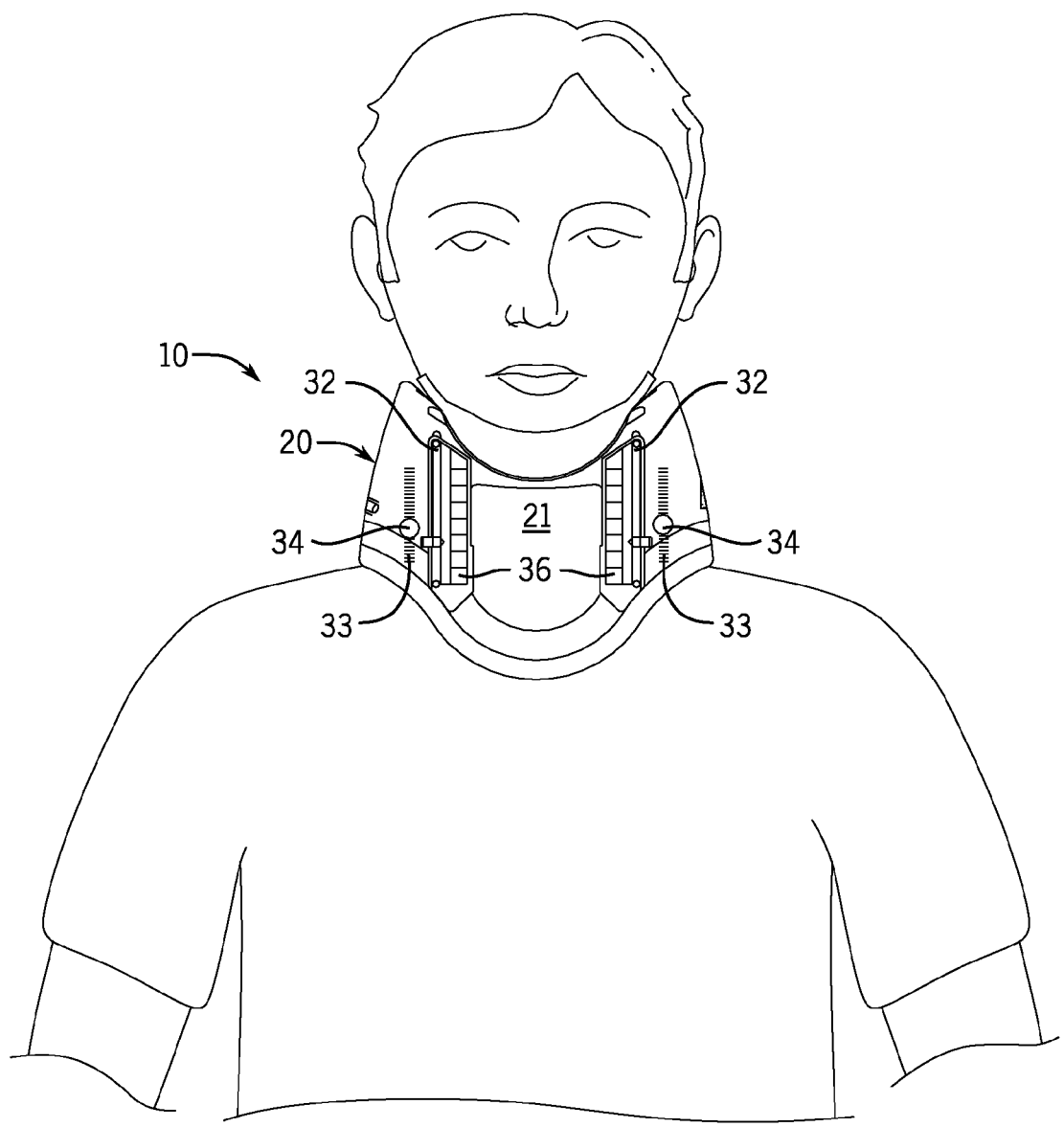
FIG. 3 is a front elevation view of the present invention in use and in a closed position.

Referring to FIGS. 1 through 3, the present invention includes a height-adjustable cervical collar 10 (c-collar). The c-collar 10 wraps around a person's neck and may be held together by a connector 18. The c-collar 10 may include an anterior side 12, a posterior side 14, lateral sides, an upper portion, and a lower portion. The present invention may include a height adjustable piece 16 to adjust the height of the overall c-collar 10. A chin and jaw support 15 are connected to the upper portion on the anterior side 12. The chin and jaw support 15 may be a strong plastic and may support the patient's chin and jaw and restrict lateral movement. The present invention may further include a posterior-lateral pocket 26. Tubing 28 may lead into the pocket 26 so that a gas or liquid may be injected into the pocket 26.

In certain embodiments, the collar 10 of the present invention may include one assembled, continuous piece of bendable plastic that wraps around the neck of a user. The anterior side 12 may be formed of two connected pieces that are adjustable in height. An airway open space 21 may be on the anterior side 12 below the chin and jaw support 15. This allows for airway management to include up to a tracheotomy with approximately but not necessarily 90 degree anterior open access space. The chin and jaw support 15 may be made of plastic and may be curved to fit the chin. The chin and jaw support 15 may attach to the upper portion of the anterior side 12 of the c-collar 10. It ranges in length from approximately, but not limited to, about 4 in to about 8 in. It ranges in width from approximately, but not limited to, about 0.5 in to about 2 in including the foam 30. Ventilation holes 24 or rectangles may allow for air movement for patient comfort.

In certain embodiments, a thin foam lining 30 may be applied to the inside of the c-collar 10 on the side that has direct contact with the patient's skin. The foam 30 may be a viscoelastic polyurethane foam. The foam 30 covers the inside plastic and is approximately, but not limited to, about 0.125 in to about 0.5 in thick. The foam lining 30 may cover the chin and jaw support 15. The foam 30 around the chin and jaw support 15 is approximately, but not limited to, about 0.5 in to about 2 in thick, with the thickest part of the foam 30 on the lateral sides of the jaw. The foam 30 on the chin and jaw support 15 is moldable and can form to the patient's mandibular or facial anatomy. The thin sheet of foam 30 may be adhered with glue, tape, Velcro®, plastic, bolts, or any other adhesives to the c-collar 10 and extends beyond the plastic borders for patient comfort.

As mentioned above, the present invention includes a height adjustable piece 16. The c-collar 10 is adjustable in height to accommodate per person's individual neck height or length of cervical spine. The c-collar 10 will adjust approximately, but not limited to, up to about 8 inches additional from its smallest and most compact size. The height adjustable piece 16 may be attached to the collar 10 by a plastic connection, bolt, adhesive, or other type of connection that would keep the two pieces together as one unit, but also works to allow a sliding motion for the height adjustable piece 16 of the anterior side 12 between the upper and lower portions. These two lower and upper pieces are adjustable in height through an open slot 32. Locking tabs 34 may be operably connected to the height adjustable piece 16 and may move the height adjustable piece 16 up and down along the open slot 32. The notches 33 may secure the locking tabs 34 in place. In certain embodiments, there may be a numbering and/or color system 36 marking the size or range of the c-collar 10 for fitting and documentation purposes. Each color and/or number range 36 may have additional smaller sizes, or micro adjustments, able to be notched or kept in place for finer or smaller adjustments.

The connector 18 of the present invention secures the collar 10 to the user's neck. In certain embodiments, the connector 18 may include a strap 18a with a mating connection that may be connected with a body mating connection 18b on the collar 10 itself. For example, the strap 18a may include a hook component of a hook and loop fastener and the body mating connection 18b may be the loop component of a hook and loop fastener. However, the connector 18 is not limited to Velcro®, and may include buttons, snap buttons, clips and the like. The strap 18a may be an approximately, but not limited to, about 1 in to about 2 in wide and about 4 in to about 8 in long adhesive strip extending out from the posterior side 14 of the c-collar 10.

In certain embodiments, the present invention may include a pocket 26. The pocket 26 may be a thin piece of plastic that is capable of being filled with approximately, but not limited to, about 500 ml of a space voiding gas or liquid, such as air. The gas or liquid may be air, a gel, foam, water, saline, or other substance able to be inserted or removed from the posterior pocket 26. The posterior pocket 26 may be a rectangular shape with a length of approximately, but not limited to, about 3 in to about 8 in and width of approximately, but not limited to, about 1 in to about 4 in. The posterior pocket 26 may contain a channel with tubing for the applied gas or liquid to enter into the posterior pocket 26 for it to inflate based on the amount of free space necessary to void between the back of the c-collar 10 and patient's posterior to lateral neck. The pocket 26 is able to extend up to 270 degrees around the posterior-lateral neck allowing for the open anterior space of 90 degrees.

The posterior-lateral pocket 26 may be adhered to the posterior portion 14 and extends to the lateral sides of the c-collar. The pocket 26 may be adhered by glue, but can be adhered with other permanent bonding substances that does not hinder the quality of the pocket filling or expanding. Directly connected to the posterior pocket may be the tubing 28 that carries the gas or liquid inserted at the end adaptor inlet 40 and travels into the pocket 26. A syringe or similar device may be applied to the end adaptor inlet 40. The gas or liquid to fill or expand the pocket 26 travels through the tubing 28, protected by a recessed channel in the plastic of the c-collar, and fills the pocket 26.

The tubing 28 may be plastic that extends from the posterior pocket 26 and through a chamber or groove on the posterior side 14, and out to the front anterior portion 12 of the c-collar 10. The tubing 28 may lie inside of the channel and the channel is recessed into the plastic of the c-collar 10 to protect the tubing 28 leading to the end adaptor inlet 40 and pocket 26. The end adaptor inlet 40 may be located at the end of the channel tubing 28 and allows the provider to adjust the specific amount of gas or liquid inserted or removed from the c-collar 10. The end adaptor inlet 40 to the tubing 28 may be made of a hard plastic that allows for the connection of the syringe-like device to control the amount of gas or liquid added or removed from posterior-lateral pocket.

The tubing holders 22 may include a hard plastic piece that has a notch, or hook intended to hold oxygen or capnography tubing 28 on the left and right side of the chin and jaw piece at the top anterior side 12 of the c-collar 10. It is approximately, but not limited to, about a half inch diameter. The tubing holders 22 may be two plastic projections, which could also be made from metal, or other hard or solid material.

The syringe or device capable of adding and removing the gas or liquid from the end adaptor inlet and tubing to and from the posterior-lateral pocket may not be connected to the c-collar 10 and can be packaged with the c-collar 10 in the same containment packaging, or be separate. The device may be used to insert and remove the gas or liquid from the posterior-lateral pocket. However, the c-collar 10 of the present invention may also include a pump and release valve directly connected to the c-collar 10 to pump up and deflate the pocket 26.

The c-collar is made from pliable or bendable plastic that allows the c-collar to be wrapped around the patient's neck as to accomplish cervical spinal motion restriction. The c-collar may be fitted appropriately for height, and height is measured and adjusted by the provider or person applying the c-collar.

The c-collar may be measured to fit where the chin is supported in a neutral position and properly secured with the Velcro® or other connector to secure the cervical collar around the patient's neck. The two height securing tabs lock the c-collar height into place. These two tabs are pulled out of the notch. The top and bottom pieces on the anterior side, which are held together as one adjustable piece, slide up and down to make the c-collar shorter or taller to fit the patient. There may be a color and/or number scale on the front of the c-collar as part of the height adjustment to mark the patient's size. The two height securing tabs are then pushed back in to lock the height of the c-collar in place. No adjustments may be required at the chin and jaw piece as the moldable foam may displace or molded to fit around the patient's mandibular anatomy preventing lateral motion of the head and neck. The syringe or device that connects to the end of the channel with end adaptor inlet to fill the pocket with the gas or liquid may then be applied and the gas or liquid may travel into the pocket until slight resistance is felt by the provider. This resistance is felt when the pocket is inflated against the patient's neck. If over-inflation occurs, the device to add or remove the gas or liquid, or syringe, can be used to remove the gas or liquid from the pocket using the same channel end adaptor inlet and pulling back on the syringe or device. The pocket may then remain adhered to the posterior and lateral portions of the c-collar but is now inflated to fill the space or void against the patient's neck, which may be individually adjusted per patient.

In certain embodiments, the c-collar may include two separate pieces: one solid anterior piece and one solid posterior piece having the posterior-lateral pocket and channel tubing still adhered and coming from the posterior piece, with the moldable or formable foam on the chin located on the anterior piece, keeping the integrity of the c-collar in cervical spinal motion restriction. The anterior and posterior portions may be applied to the neck and adhered or strapped together on the lateral sides of the neck holding the two pieces together on the patient.

A person may use the present invention for anyone requiring cervical spinal motion restriction. One person may place the c-collar on the patient. The cervical collar may be measured by the provider applying the c-collar on the patient so the head and neck are supported in a neutral position. Once the provider measures the neck and adjusts the height of the c-collar, the provider may lock the c-collar in place with the notches at the height adjuster and can record appropriately the number and/or color of the size the c-collar placement. The chin rests on the foam of the chin piece, and the foam molds around the patient's chin and jaw, preventing lateral, flexion and extension motions of the head and neck. Once properly measured and fitted and wrapped around the patient's neck, the c-collar is then adhered or secured by the Velcro®, or adhesive strap, to keep the c-collar in place around the patient's neck. The syringe, or a device to add the gas or liquid, is applied to the end adaptor inlet of the channel tubing and the gas or liquid is pushed in through the adaptor inlet, travels through the channel tubing and into the posterior-lateral pocket, causing the pocket to fill or expand. The gas or liquid is placed into the c-collar until slight resistance is felt when filling, or inflating the pocket. This slight resistance is felt when the posterior-lateral pocket successfully voids the space between the flat posterior and lateral portions of the c-collar and the patient's cervical spine. The device to add the gas or liquid, or the syringe, is removed from the end adaptor inlet and the gas or liquid remains in the posterior pocket. If gas or liquid needs to be removed, or the posterior-lateral pocket is overinflated, the syringe or device to add or remove the gas or liquid is reapplied to the end adaptor inlet of the channel tubing and the syringe or device can pull out, remove, or withdraw the gas or liquid by pulling back on the plunger of the syringe, causing the posterior-lateral pocket to reduce in size or deflate. The c-collar is now properly measured, applied and secured around the neck, and posterior pocket inflated preventing lateral, and flexion and extension motions of the neck for successful cervical spinal motion restriction.

It should be understood, of course, that the foregoing relates to exemplary embodiments of the invention and that modifications may be made without departing from the spirit and scope of the invention as set forth in the following claims.

What is claimed is:

1. A cervical collar comprising:
   a body comprising an anterior side, a posterior side, and lateral sides, an upper portion and a lower portion, wherein the body is configured to wrap around a user's neck;
   a connector releasably attaching the anterior side and the posterior side;
   a chin support formed at the upper portion of the anterior side;
   a viscoelastic polyurethane foam lining the chin support; and
   an inflatable pocket formed on the body of the cervical collar.

2. The cervical collar of claim 1, wherein the inflatable pocket is formed on at least one of the posterior and lateral sides.

3. The cervical collar of claim 2, wherein the tubing is embedded within the body of the cervical collar and wherein the inlet forms an end adapter inlet at a surface of the body.

4. The cervical collar of claim 1, further comprising a tubing comprising a first end and a second end, wherein the first end is attach to an entrance of the inflatable pocket and the second end forms an inlet configured to receive at least one of a gas and a liquid that flows through the tubing and inflates the inflatable pocket.

5. The cervical collar of claim 4, wherein the end adapter inlet is configured to receive a syringe.

6. The cervical collar of claim 1, wherein the chin support comprises a top end and a bottom end, wherein the foam tapers from the top end to the bottom end.

7. The cervical collar of claim 6, wherein a thickest portion of the foam is at the top end.

8. The cervical collar of claim 1, wherein the body is adjustable in height.

9. A method of securing a cervical collar to a patient comprising:
   providing a cervical collar comprising a body comprising an anterior side, a posterior side, and lateral sides with an inflatable pocket formed on at least one of the posterior and lateral sides, a chin support formed at the upper portion of the anterior side, and a viscoelastic polyurethane foam lining the chin support;
   wrapping the body of the cervical collar around a user's neck and connecting the anterior side and the posterior side together; and
   inflating the pocket with at least one of a gas and a liquid, wherein the pocket is inflated so that the body of the cervical collar is pressing against the user's neck.

* * * * *